United States Patent
Otsubo et al.

[11] Patent Number: 6,146,367
[45] Date of Patent: Nov. 14, 2000

[54] TRAINING PANTS FOR INFANTS

[75] Inventors: Toshifumi Otsubo, Kagawa-ken; Hideaki Kitaoka, Tokyo, both of Japan

[73] Assignee: Uni-Charm Corporation, Ehime-ken, Japan

[21] Appl. No.: 09/256,076

[22] Filed: Feb. 24, 1999

[30] Foreign Application Priority Data

Feb. 24, 1998  [JP]  Japan .................................. 10-042609

[51] Int. Cl.⁷ .................................................. A61F 13/15
[52] U.S. Cl. ...................................................... 604/385.1
[58] Field of Search ........................... 604/385.1, 385.2, 604/378, 384, 396

[56] References Cited

U.S. PATENT DOCUMENTS

| | | | |
|---|---|---|---|
| 5,662,637 | 9/1997 | Kitaoka et al. ...................... | 604/385.2 |
| 5,695,849 | 12/1997 | Shawver et al. ................. | 604/385.1 X |
| 5,836,930 | 11/1998 | Lantz et al. .............................. | 604/378 |
| 5,865,824 | 2/1999 | Chen et al. .......................... | 604/384 X |
| 5,868,725 | 2/1999 | Coles et al. .......................... | 604/385.1 |

FOREIGN PATENT DOCUMENTS

| | | |
|---|---|---|
| 5-59601 | 3/1993 | Japan . |
| 5-59602 | 3/1993 | Japan . |

*Primary Examiner*—John B. Yasko
*Attorney, Agent, or Firm*—Lowe Hauptman Gopstein Gilman & Berner

[57] ABSTRACT

Training pants for infants include a pant body including of a topsheet, a backsheet and a water-impervious intermediate sheet disposed between the topsheet and the backsheet, and a wetness retaining sheet substantially made of hydrophilic fibers such as rayon. The wetness retaining sheet is bonded to the topsheet intermittently in longitudinal and transverse direction of the sheet. Zones of the wetness retaining sheet which are not bonded to the topsheet continuously extend in the transverse direction of the wetness retaining sheet.

11 Claims, 2 Drawing Sheets

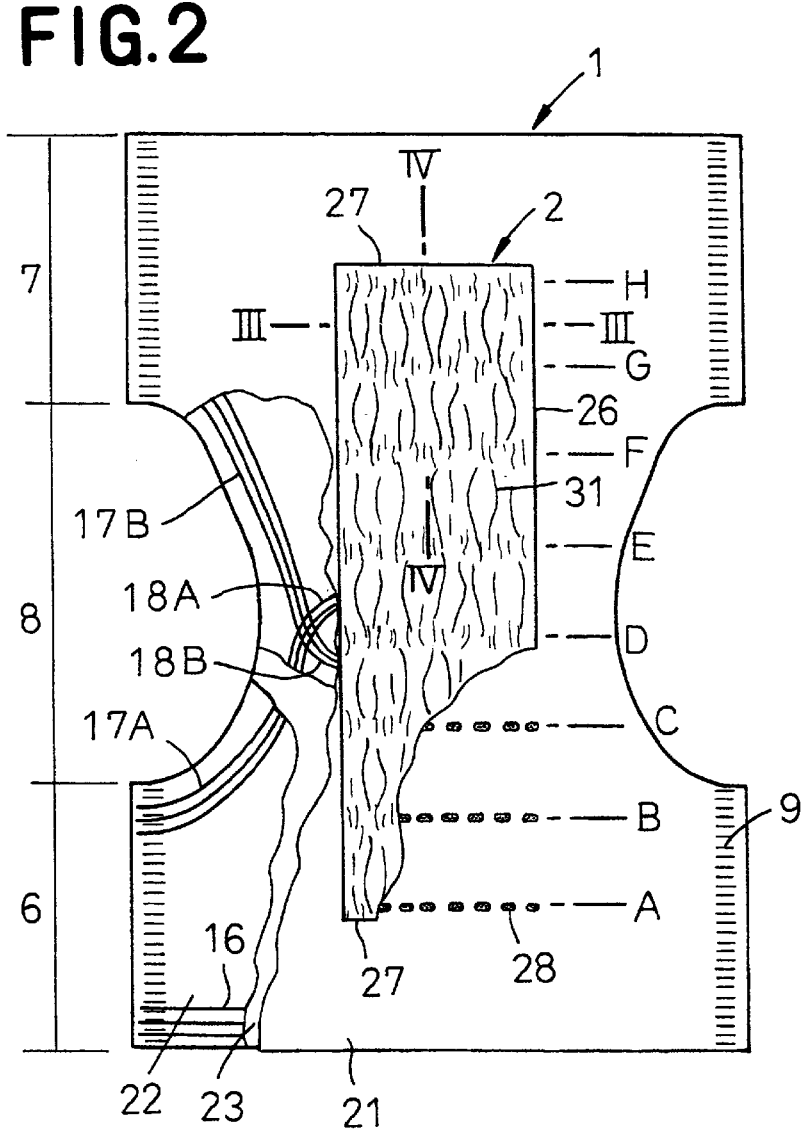
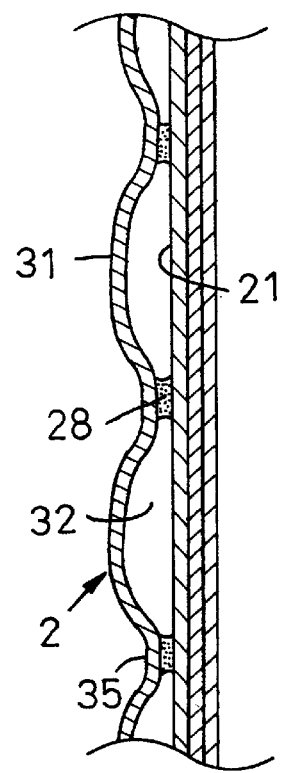
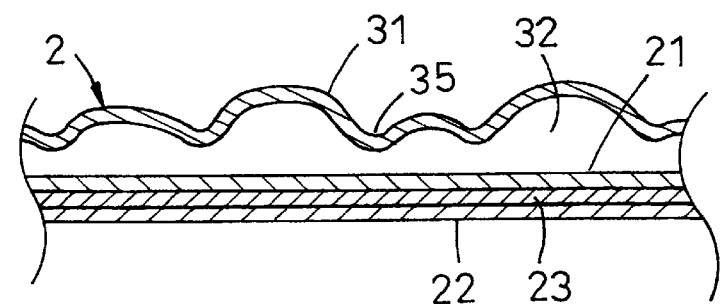

TRAINING PANTS FOR INFANTS

BACKGROUND OF THE INVENTION

This invention relates to training pants for infants which are adapted to be washed and reused.

Japanese Patent Application Disclosure Gazette (Kokai) No. Hei5-59601 discloses training pants for infants comprising a liquid-pervious topsheet, a liquid-impervious backsheet and a liquid-absorbent core disposed between these two sheets. A wetness retaining sheet is intermittently bonded to an upper surface of the topsheet in its middle zone. This wetness retaining sheet is partially raised with respect to the topsheet.

Japanese Patent Application Disclosure Gazette (Kokai) No. Hei5-59602 discloses training pants for infant comprising a liquid-pervious topsheet made of a nonwoven fabric, a liquid-impervious backsheet and a liquid-absorbent core disposed between these two sheets. The topsheet is provided in its middle zone with wetness sensing means. The wetness sensing means comprise an upper layer of nonwoven fabric being relatively high in its fiber density and a lower layer of nonwoven fabric being relatively low in its fiber density. A fiber density of the topsheet is higher than the fiber density of the lower layer and a wetting property of the wetness sensing means is higher than a wetting property of the topsheet.

In both cases as have been identified above, the liquid-absorbent core comprises a mixture of fluff pulp fibers, thermoplastic crimped fibers and discrete particles of a water insoluble hydrogel.

The training pants according to the two examples of prior art are unwashable and can not be reused once they have been used. This is for the reason that the absorbent core of fluff pulp fibers are significantly deformed and the hydrogel is liable to be gel-blocked upon water absorption whether it is due to urine-absorption or washing. The training pants of prior art as have been described are characterized by a relatively high urine-absorprition capacity. From an economical viewpoint also, it will be disadvangeously wasteful to use them for a long period continuously even after an infant has been adequately trained and an amount of urine discharged by the infant directly on the training pants has considerably decreased.

SUMMARY OF THE INVENTION

In view of the problem as has been described above, it is an object of the invention to provide economically advantageous training pants adapted to be repeatedly used for an infant having already arrived at a final stage of training.

According to the invention, there is provided training pants for infants having a front waist region, a rear waist region and a crotch region therebetween, the training pants comprising:

a pant body including a first sheet of nonwoven fabric having an inner surface and an outer surfaces;

a liquid-impermeable second sheet bonded to the outer surface of the first sheet;

a wetness retaining sheet having a transverse direction corresponding to a circumferencial direction of the pant body and a longitudinal direction orthogonal to the transverse direction and a hydrophilicity higher than that of the first sheet; and the wetness retaining sheet being intermittently bonded to the inner surface of the first sheet in the transverse direction as well as in the longitudinal direction, the remaining portions not bonded to the inner surface comprising zones continuously extending in the transverse direction and zones lifted out of the inner surface.

Preferably, the wetness retaining sheet comprises a non-woven fabric containing intrinsically hydrophilic fibers of 60≈100% by weight.

Preferably, the wetness retaining sheet is adapted to contract by 2≈20% as it is dried again after its water-absorption at least in the foregoing transversal direction.

Preferably, the pant body further comprises a third sheet of nonwoven fabric covering the outer surface of the second sheet and having a portion extending outwards beyond peripheral edges of the second sheet along which the third sheet is bonded to the first sheet.

Preferably, the first sheet has an elastic stretchability at least in the foregoing transversal direction and wherein the wetness retaining sheet is bonded to said first sheet being stretched in any one of its elastically stretchable directions and then said first sheet is released to contract so that the wetness retaining sheet forms a plurality of undulating crests lifted out of the first sheet and a plurality of troughs defined between respective pairs of adjacent crests.

Preferably, of the first sheet and third sheet, at least the first sheet comprises crimped composite fibers and individual fibers therein are mechanically intertwined to form the first sheet.

Preferably, any one of the first sheet, third sheet and wetness retaining sheet is of a nonwoven fabric obtained by a water jet fiber entangling treatment.

Preferably, the first sheet contains intrinsically hydrophilic fibers of 0≈30% by weight.

Preferably, the front and rear waist regions are placed upon each other and bonded together along their transversely opposite side edges so as to form a waist-opening and a pair of leg-openings and the pants have an elastically stretchable member extending along a peripheral edge of the waist-opening, elastically stretchable members extending along respective peripheral edges of the leg-openings and elastically stretchable members extending between the pair of leg-openings in the crotch region.

Preferably, the elastically stretchable members extending between the pair of leg-openings are bonded with a tension to the crotch region.

Preferably, the elastically stretchable members extending along the respective peripheral edges of the leg-opening are intermittently bonded to the pant body at relatively high bonding area ratio along two or more positions of the peripheral edges and at relatively low bonding area ratio along the remainder of the peripheral edges.

BRIEF DESCRIPTION OF THE DRAWINGS

FIG. 2 is a plan view showing the training pants shown in FIG. 1 with front and rear waist regions thereof separated from each other and unfolded to a flat state, as partially broken away;

FIG. 3 is a fragmentary sectional view taken along a line III—III in FIG. 1; and FIG. 4 is a fragmentary sectional view taken along a line IV—IV in FIG. 1.

DESCRIPTION OF THE PREFERRED EMBODIMENTS

Figure 1:
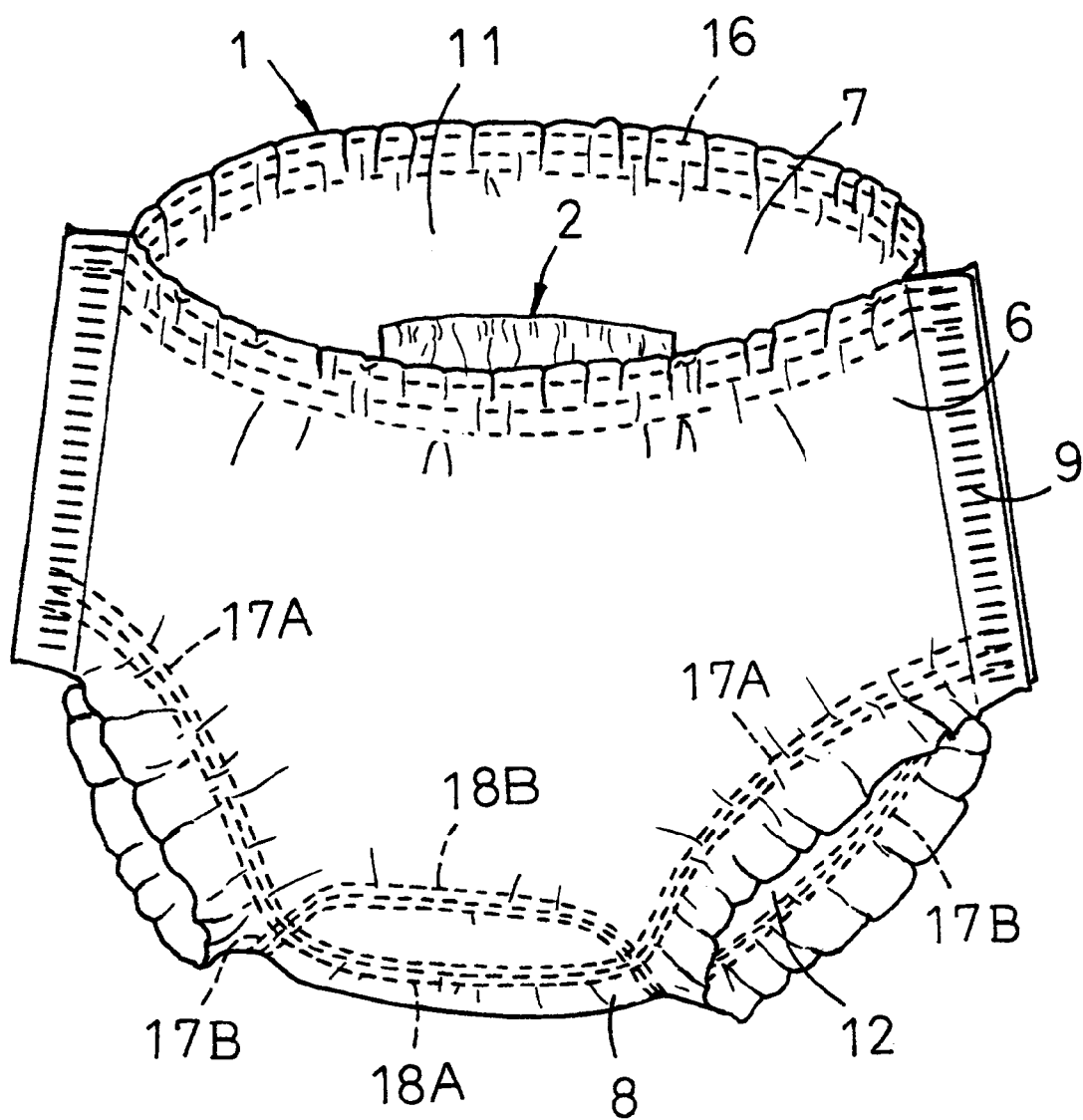
FIG. 1 is a perspective view of training pants for infants according to the invention.

Details of training pants according to the invention will be more fully understood from the description given hereunder with reference to the accompanying drawings.

Training pants shown by FIG. 1 in a perspective view generally comprise a pant body 1 and a wetness retaining sheet 2 attached to an inner surface of the pant body 1. The pant body 1 has a front waist region 6, a rear waist region 7 and a crotch region 8 extending between the front and rear waist regions 6, 7. The front and rear waist regions 6, 7 are placed flat upon each other along transversely opposite side edges of the pants and joined together at a plurality of joining lines 9 arranged intermittently in the vertical direction along each of the side edges so as to form a waist-opening 11 and a pair of leg-openings 12. The waist-opening 11 is provided with an elastic member 16 extending along its peripheral edges as indicated by broken lines in FIG. 1. Each of the leg-openings 12 is provided with a first elastic member 17A extending along approximately a front half of its peripheral edges as well as a second elastic member 17B extending along approximately a rear half of its peripheral edges. These elastic members 17A, 17B associated with one of the leg-openings 12 intersect each other in the crotch region 8, then branch off from each other to extend toward the other leg-opening 12, and intersect again each other in the crotch region 8. Then the first elastic member 17A extends approximately a front half round and the second elastic member 17B extends approximately a rear half round the other leg-opening 12 along its peripheral edge. Referring to FIG. 1, the portions of the first and second elastic members 17A, 17B extending across the crotch region 8 are designated by references 18A, 18B, respectively.

FIG. 2 is a plan view showing the training pants shown in FIG. 1 with the front and rear waist regions separated from each other along the joining zones 9 and unfolded in a flat state as partially broken away. FIGS. 3 and 4 are fragmentary sectional views taken along lines III—III and IV—IV, respectively. The pant body 1 comprises a non-hydrophilic topsheet 21, a non-hydrophilic or hydrophilic backsheet 22, and a water-impervious intermediate sheet 23 disposed between the two sheets 21, 22. The elastic member 16 associated with the waist-opening 11 extends between the backsheet 22 and the intermediate sheet 23 and is secured under appropriate tension to at least one of these two sheets 22, 23. The first and second elastic members 17A, 17B associated with the pair of leg-openings 12 extend also between the backsheet 22 and the intermediate sheet 23 and are secured under appropriate tension to at least one of these two sheets 22, 23 at least along the peripheral edges of the respective leg-openings 12. The portions 18A, 18B of the first and second elastic members 17A, 17B extending between the pair of leg-openings 12 may be secured or not to at least one of the two sheets 22, 23 with or without appropriate tension.

The wetness retaining sheet 2 can absorb and retain a quantity of urine discharged thereon with a hydrophilicity higher than that of the topsheet 21. While no limitation is imposed upon a plane shape of this sheet 2, it is preferable for this sheet 2 to have a substantially rectangular plane shape, as in the illustrated embodiment. The wetness retaining sheet 2 according to this embodiment is defined by longitudinally opposite ends 27 extending transversely of the pant body 1 and transversely opposite side edges 26 extending orthogonally to the ends 27 extending from the crotch region 8 toward the front and rear waist regions 6, 7. The wetness retaining sheet 2 is partially bonded to the topsheet 21 by means of water-proof adhesive agent 28 such as hot melt adhesive intermittently applied on the topsheet 21 transversely as well as longitudinally of the pant body 1. In the case of the illustrated embodiment, the adhesive agent 28 is intermittently applied on a plurality of imaginary lines A, B, C, . . . , H extending in parallel one to another transversely of the pant body 1.

As will be apparent from FIGS. 3 and 4, portions of the wetness retaining sheet 2 left free from being bonded to the topsheet 21 are raised with respect to the topsheet so as to form a plurality of crests 31 undulating longitudinally of the pant body 1. Between each pair of adjacent imaginary lines A, B, C, . . . , H, the wetness retaining sheet 2 can be spaced apart from the topsheet 21 to form gaps 32 extending across the wetness retaining sheet 2 between the wetness retaining sheet 2 and the topsheet 21. To realize such crests 31 formed by the wetness retaining sheet 2, this wetness retaining sheet 2 may be bonded to the topsheet 21 being maintained under elastic tension transversely of the pant body 1, provided that the topsheet 21 is elastically stretchable in such direction, and thereafter the topsheet 21 may be released to contract. The gaps 32 may be obtained merely by bonding the wetness retaining sheet 2 to the topsheet 21 having the adhesive 28 applied thereon as illustrated in FIG. 2. However, it is preferred to bond the wetness retaining sheet 2 to the topsheet 21 being maintained under elastic tension longitudinally of the pant body 1, provided that the topsheet 21 is elastically stretchable in the foregoing direction, and thereafter to release the topsheet to contract, since a distance by which the wetness retaining sheet 2 is spaced apart from the topsheet 21 in the respective gaps 32 can be thereby enlarged in a thickness direction of the pants 1. Preferably, the wetness retaining sheet 2 is bonded to the topsheet 21 being maintained under tension corresponding to a stretch ratio of 1.1≈1.5 transversely or both transversely and longitudinally of the pant body 1.

Of the training pants arranged as has been described above, the topsheet 21 may be formed by a nonwoven fabric comprising hydrophobic thermoplastic synthetic fibers of 60≈100% by weight and hydrophilic fibers of 40≈0% by weight and having a basis weight of 15≈100 g/m². The synthetic fibers may be conjugated fibers of side-by-side type or sheath/core type while the hydrophilic fibers may be either rayon, acetate or the like which is intrinsically hydrophilic or hydrophobic synthetic fibers treated so as to have desired hydrophilicity. Preferably the nonwoven fabric is an elastically stretchable nonwoven fabric which is obtained by transforming a web comprising the synthetic fibers and hydrophilic fibers to a nonwoven fabric under the well known water jet fiber entangling treatment and by heat-treating this nonwoven fabric to crimp the conjugated fibers. The topsheet 21 obtained in this manner makes it possible not only to form a soft touch body surface but also to have a sweat-absorbent property so far as the topsheet 21 contains the hydrophilic fibers.

The backsheet 22 may be formed by a nonwoven fabric substantially similar to the foregoing nonwoven fabric for the topsheet 21. If it is not required for the backsheet 22 to have a sweat-absorbent property as high as such property presented by the topsheet 21, the backsheet 22 may be formed by an elastically stretchable nonwoven fabric comprising crimped conjugated fibers of 100% by weight.

For the intermediate sheet 23, a water-impervious thermoplastic synthetic resin sheet, more preferably, a breathable water-impervious thermoplastic synthetic resin sheet may be used. This sheet 23 may be substantially identical to any one of the topsheet 21 and the backsheet 22 in shape as well as in size or larger than the wetness retaining sheet 2 and smaller than both the topsheet 21 and the backsheet 22.

The wetness retaining sheet 2 may be formed by a nonwoven fabric comprising intrinsically hydrophilic fibers such as rayon or acetate of 80≈100% by weight and thermoplastic synthetic fibers of 20≈0% by weight. Such nonwoven fabric preferably has a shrinkage percentage of 2≈20% as measured after it has been immersed in water for 30 min. and then dried. The nonwoven fabric having such shrinkage percentage has its dimensions progressively decreased as its washing is repeated and consequently the presence of the undulating crests 31 progressively becomes remarkable.

The training pants according to the invention adopts hydrophilic fibers such as rayon fibers for the wetness retaining sheet 2 so that the pants soiled with urine can be effectively washed and reused. Such wetness retaining sheet 2 is free from deterioration of its hydrophilicity due to washing, which can not be avoided by the wetness retaining sheet adopting hydrophobic fibers having its surface treated to become hydrophilic. The wetness retaining sheet 2 made of a nonwoven fabric obtained by the well known water jet fiber entangling treatment is advantageous in also that such sheet is less liable to become fluffy even after washing. Of the pant body 1, the sheets used for the topsheet 21 and the backsheet 22 as well as the intermediate sheet 23 have a strength enough to stand once or twice or several times of washing. Furthermore, heat-sealing technique or water-proof adhesive agent are used for bonding of these sheets 21, 22, 23 so that these sheets are not readily separated one from another even when these sheets are washed.

It is desired to assure a high durability of the pant body 1 against repeated washing. As one of preferred measures to achieve this, the sheets placed upon each other are intermittently bonded together at a relatively high bonding area ratio along at least predetermined portions of the edges, i.e., the transversely opposite side edges of the pants as well as the peripheral edges of the waist-opening and the leg-openings in order to improve a peel strength of these sheets. At the same time, these sheets are bonded together at a relatively low bonding area ratio over a region of the pants extending inside the edges in order to prevent these sheets from becoming unacceptably rigid over this region. As the another preferred measure, the elastic members 16, 17A, 17B are intermittently secured to the topsheet and/or the backsheet 22 along the peripheral edges of the waist-opening 11 and the leg-opening 12 at respective bonding area ratios which are locally higher along the respective peripheral edges. Particularly in the case of the elastic members 17A, 17B, the bonding area ratio for each of them is preferably adjusted to be relatively high in the proximity of the uppermost point of the leg-opening 12 as well as in the crotch region 8 and to be relatively low in the remaining region so that the intrinsic elasticity of the member should not be restrained. With the embodiment in which the elastic members 17A, 17B intersect each other in the crotch region 8, the bonding area ratio is preferably adjusted to be relatively high in the proximity of the intersection.

The wetness retaining sheet 2 is able to absorb and retain a quantity of urine discharged thereon not only by itself but also to retain an additional quantity of urine by troughs defined between each pair of adjacent undulating crests 31 lifted out from the topsheet 21 as well as by the gaps 32 defined between the crests 31 and the topsheet 21. Thus the wetness retaining sheet 2 is able to give the wearer a discomfortable feeling. Particularly the quantity of urine retained by the troughs 35 completely surrounded by the undulating crests 31 can not easily run out of the wetness retaining sheet 2 and therefore can emphasize the discomfortable feeling.

The portions 18A, 18B of the elastic members 17A, 17B which extend across the crotch region 8 of the pants effectively function to prevent the crotch region 8 of the pants from hanging down, i.e., to prevent the wetness retaining sheet 2 from being spaced apart from the wearer's crotch region inclusive of the perineum and the proximity thereof. The portions 18A, 18B facilitate the wetness retaining sheet 2 to be maintained in close contact with the wearer's crotch region so as to give the wearer a distinctly discomfortable feeling even when a quantity of urine discharged is relatively small and thereby to improve the training effect. Such effect realized by these portions 18A, 18B is further improved when the portions 18A, 18B are under tension.

The training pants of such arrangement is particularly suitable to be used for a late period of training because a quantity of urine discharged by an infant become relatively small after the training has proceeded to its final stage.

The used and washed pants can be rapidly dried because the wetness retaining sheet 2 is partially lifted out of the topsheet 21 to maintain a good ventilation between the retaining sheet 2 and the topsheet 21. These sheets 2, 21 placed upon each other can be rapidly dried particularly because the zones of the retaining sheet 2 which are not bonded to the topsheet 21 extend entirely across the width of the retaining sheet 2 and this width is smaller than the length thereof. These zones not bonded to the topsheet 21 facilitate the ventilation which is necessary to dry the washed pants as rapidly as possible.

The training pants according to the invention comprise the component sheets bonded together by means of water-proof adhesive agent and the fibers itself as essential material for the wetness retaining sheet is hydrophilic. Such feature makes it possible to wash and reuse the training pants.

The wetness retaining sheet has the non-bonded zones extending entirely across its width of which the dimension is smaller than the dimension of its length. Such feature promotes the ventilation between the wetness retaining sheet and the topsheet, making it possible to dry the washed pants as rapidly as possible.

The wetness retaining sheet is preferably adapted to contract by 2≈20% as it is dried again after it has absorbed water. With the wetness retaining sheet having such property, the undulating crests become more and more noticeable as washing is repeated. Consequently, the wetness retaining sheet can be more reliably placed against the wearer's skin and emphasize an discomfortable feeling when urination occurs. In addition, the distance by which the undulating crests are spaced apart from the topsheet is enlarged and a ventilation necessary to dry the washed training pants is also improved.

The embodiment of the training pants in which the elastic members extend across the crotch region can ensure the desired training effect even when a discharged quantity of urine is relatively small. This is for the reason that the elastic members function to prevent the crotch region of the pants from hanging down and thereby to keep the wetness retaining sheet in close contact with the wearer's crotch region.

What is claimed is:

1. Training pants for infants having a front waist region, a rear waist region and a crotch region therebetween, said training pants comprising:
    a pant body including a first sheet of nonwoven fabric having an inner surface and an outer surfaces;
    a liquid-impermeable second sheet bonded to the outer surface of said first sheet;
    a wetness retaining sheet having a transverse direction corresponding to a circumferencial direction of said pant body and a longitudinal direction orthogonal to said transverse direction and a hydrophilicity higher than that of said first sheet; and said wetness retaining sheet being intermittently bonded to the inner surface of said first sheet in said transverse direction as well as in said longitudinal direction, the remaining portions not bonded to said inner surface comprising zones continuously extending in said transverse direction and zones lifted out of said inner surface.

2. The training pants according to claim 1, wherein said wetness retaining sheet comprises a nonwoven fabric containing intrinsically hydrophilic fibers of 60≈100% by weight.

3. The training pants according to claim 1, wherein said wetness retaining sheet is adapted to contact by 2≈20% when it is dried again after its water-absorption at least in said transverse direction.

4. The training pants according to claim 1 wherein said pant body further comprises a third sheet of nonwoven fabric covering the outer surface of said second sheet and having a portion extending outward beyond peripheral edges of said second sheet along which said third sheet is bonded to said first sheet.

5. The training pants according to claim 1, wherein said first sheet has an elastic stretchability at least in said transverse direction and wherein said wetness retaining sheet is bonded to said first sheet being under tension in any one of its elastically stretchable directions and then said first sheet is released to contract so that said wetness retaining sheet forms a plurality of undulating crests lifted out of said first sheet and a plurality of troughs defined between respective pairs of adjacent crests.

6. The training pants according to claim 1, wherein, of said first sheet and third sheet, at least said first sheet comprises crimped composite fibers and individual fibers therein are mechanically entangled to form said first sheet.

7. The training pants according to claim 1, wherein one of said first sheet, third sheet and wetness retaining sheet is of nonwoven fabrics obtained by a water jet fiber entangling treatment.

8. The training pants according to claim 1, wherein said first sheet contains intrinsically hydrophilic fibers of 0≈30% by weight.

9. The training pants according to claim 1, wherein said front and rear waist regions are placed upon each other and bonded together along their transversely opposite side edges so as to form a waist-opening and a pair of leg-openings and said pants have an elastically stretchable member extending along peripheral edges of said waist-opening, elastically stretchable members extending along respective peripheral edges of the leg-openings and elastically stretchable members extending between the pair of leg-openings in said crotch region.

10. The training pants according to claim 9, wherein the elastically stretchable members extending between said pair of leg-openings are bonded under tension to said crotch region.

11. The training pants according to claim 9, wherein the elastically stretchable members extending along the respective peripheral edges of said leg-openings are intermittently bonded to said pant body at relatively high bonding area ratio along two or more positions of said peripheral edges and at relatively low bonding area ratio along the remainder of said peripheral edges.

* * * * *